United States Patent
Hamman

(10) Patent No.: US 8,758,376 B2
(45) Date of Patent: Jun. 24, 2014

(54) SYSTEM AND METHOD FOR ATTACHING A VEIN, AN ARTERY, OR A TUBE IN A VASCULAR ENVIRONMENT

(75) Inventor: Baron L. Hamman, Dallas, TX (US)

(73) Assignee: Castlewood Surgical, Inc., Dallas, TX (US)

( * ) Notice: Subject to any disclaimer, the term of this patent is extended or adjusted under 35 U.S.C. 154(b) by 865 days.

(21) Appl. No.: 12/235,469

(22) Filed: Sep. 22, 2008

(65) Prior Publication Data
US 2009/0018555 A1 Jan. 15, 2009

Related U.S. Application Data

(62) Division of application No. 11/084,453, filed on Mar. 18, 2005, now Pat. No. 7,763,037.

(51) Int. Cl.
*A61B 17/04* (2006.01)

(52) U.S. Cl.
USPC .............................. 606/153; 606/148; 606/198

(58) Field of Classification Search
USPC ............ 606/108, 139–156, 198; 600/36, 587; 623/23.72
See application file for complete search history.

(56) References Cited

U.S. PATENT DOCUMENTS

| 4,222,380 | A |   | 9/1980  | Terayama |
| 4,553,542 | A | * | 11/1985 | Schenck et al. ............... 606/153 |
| 4,553,543 | A |   | 11/1985 | Amarasinghe |
| 4,622,970 | A |   | 11/1986 | Wozniak |
| 4,770,176 | A |   | 9/1988  | McGreevy et al. |
| 4,827,940 | A |   | 5/1989  | Mayer et al. |
| 4,836,596 | A |   | 6/1989  | Owen |
| 4,911,164 | A |   | 3/1990  | Roth |
| 5,042,161 | A | * | 8/1991  | Hodge ....................... 33/501.45 |
| 5,053,041 | A |   | 10/1991 | Ansari et al. |
| 5,480,407 | A |   | 1/1996  | Wan et al. |
| 5,542,937 | A |   | 8/1996  | Chee et al. |

(Continued)

FOREIGN PATENT DOCUMENTS

| CN | 120630153 A | 8/2012 |
| JP | 2003532457 | 11/2003 |

(Continued)

OTHER PUBLICATIONS

Notification of Transmittal of the International Search Report and the Written Opinion of the International Searching Authority, or the Declaration (1 page), International Search Report (6 pages), and Written Opinion (8 pages) for International Application No. PCT/US2010/052253 mailed Jan. 26, 2011.

(Continued)

*Primary Examiner* — Kathleen Holwerda
(74) *Attorney, Agent, or Firm* — Patent Capital Group

(57) ABSTRACT

A device for assisting in a vascular procedure is provided that includes a handle and one or more legs that are operable to move in response to a force being applied to the handle. The legs are operable to extend and to contract in order to manipulate a conduit. In a more particular embodiment, the device can be used in conjunction with a stand operable to receive the conduit such that the conduit can be removed from the stand by the device. The stand may include one or more graduations that indicate the size of the conduit once it is positioned on the stand.

13 Claims, 11 Drawing Sheets

(56) References Cited

U.S. PATENT DOCUMENTS

| | | |
|---|---|---|
| 5,554,162 A | 9/1996 | DeLange |
| 5,643,254 A | 7/1997 | Scheldrup et al. |
| 5,669,905 A | 9/1997 | Scheldrup et al. |
| 5,868,763 A | 2/1999 | Spence et al. |
| 5,904,697 A | 5/1999 | Gifford, III et al. |
| 5,944,728 A | 8/1999 | Bates |
| 6,019,722 A | 2/2000 | Spence et al. |
| 6,030,370 A | 2/2000 | Kupka et al. |
| 6,074,401 A | 6/2000 | Gardiner et al. |
| 6,113,612 A | 9/2000 | Swanson et al. |
| 6,149,658 A | 11/2000 | Gardiner et al. |
| 6,165,186 A | 12/2000 | Fogarty et al. |
| 6,193,734 B1 | 2/2001 | Bolduc et al. |
| 6,206,827 B1 | 3/2001 | Chin et al. |
| 6,224,619 B1 | 5/2001 | Hill |
| 6,251,092 B1 | 6/2001 | Qin et al. |
| 6,309,416 B1 | 10/2001 | Swanson et al. |
| 6,352,543 B1 | 3/2002 | Cole |
| 6,358,258 B1* | 3/2002 | Arcia et al. .................. 606/139 |
| 6,368,341 B1 | 4/2002 | Abrahamson |
| 6,371,964 B1 | 4/2002 | Vargas et al. |
| 6,440,163 B1 | 8/2002 | Swanson et al. |
| 6,508,822 B1 | 1/2003 | Peterson et al. |
| 6,514,265 B2 | 2/2003 | Ho et al. |
| 6,517,558 B2 | 2/2003 | Gittings et al. |
| 6,533,812 B2 | 3/2003 | Swanson et al. |
| 6,551,314 B1 | 4/2003 | Hill et al. |
| 6,551,332 B1 | 4/2003 | Nguyen et al. |
| 6,565,582 B2 | 5/2003 | Gifford, III et al. |
| 6,575,985 B2 | 6/2003 | Knight et al. |
| 6,605,104 B2 | 8/2003 | Sato et al. |
| 6,607,541 B1 | 8/2003 | Gardiner et al. |
| 6,613,059 B2 | 9/2003 | Schaller et al. |
| 6,616,675 B1 | 9/2003 | Evard et al. |
| 6,620,177 B2 | 9/2003 | Buelna et al. |
| 6,635,214 B2 | 10/2003 | Rapacki et al. |
| 6,641,593 B1 | 11/2003 | Schaller et al. |
| 6,652,540 B1 | 11/2003 | Cole et al. |
| 6,660,015 B1 | 12/2003 | Berg et al. |
| 6,673,085 B1 | 1/2004 | Berg |
| 6,695,859 B1 | 2/2004 | Golden et al. |
| 6,699,256 B1 | 3/2004 | Logan et al. |
| 6,699,257 B2 | 3/2004 | Gifford, III et al. |
| 6,702,829 B2 | 3/2004 | Bachinski et al. |
| 6,719,768 B1 | 4/2004 | Cole et al. |
| 6,723,038 B1 | 4/2004 | Schroeder et al. |
| 6,730,103 B2* | 5/2004 | Dakov .................... 606/153 |
| 6,743,169 B1 | 6/2004 | Taylor et al. |
| 6,743,170 B1 | 6/2004 | Spence et al. |
| 6,802,847 B1 | 10/2004 | Carson et al. |
| 6,802,848 B2 | 10/2004 | Anderson et al. |
| 6,808,498 B2 | 10/2004 | Laroya et al. |
| 6,814,743 B2 | 11/2004 | Chin et al. |
| 6,960,217 B2 | 11/2005 | Bolduc |
| 7,001,401 B1 | 2/2006 | Castaneda et al. |
| 7,063,711 B1 | 6/2006 | Loshakove et al. |
| 7,112,211 B2 | 9/2006 | Gifford, III et al. |
| 7,122,040 B2 | 10/2006 | Hill et al. |
| 7,150,742 B2 | 12/2006 | Takamoto et al. |
| 7,212,870 B1 | 5/2007 | Helland |
| 7,294,139 B1 | 11/2007 | Gengler |
| 7,425,219 B2 | 9/2008 | Quadri |
| 7,763,037 B2 | 7/2010 | Hamman |
| 7,776,062 B2 | 8/2010 | Besselink et al. |
| 8,029,519 B2 | 10/2011 | Breton et al. |
| 8,486,094 B2 | 7/2013 | Hamman |
| 2001/0001826 A1 | 5/2001 | Bolduc et al. |
| 2002/0022852 A1* | 2/2002 | Dakov .................... 606/153 |
| 2002/0077636 A1 | 6/2002 | Arcia et al. |
| 2003/0120291 A1 | 6/2003 | Chin et al. |
| 2003/0125755 A1 | 7/2003 | Schaller et al. |
| 2003/0176878 A1 | 9/2003 | Bolduc et al. |
| 2003/0208214 A1* | 11/2003 | Loshakove et al. ........... 606/153 |
| 2004/0068276 A1 | 4/2004 | Golden et al. |
| 2004/0087985 A1 | 5/2004 | Loshakove et al. |
| 2004/0127919 A1 | 7/2004 | Trout et al. |
| 2005/0043749 A1 | 2/2005 | Breton et al. |
| 2005/0070924 A1* | 3/2005 | Schaller et al. ................ 606/142 |
| 2005/0267498 A1 | 12/2005 | Hendricksen et al. |
| 2005/0277958 A1 | 12/2005 | Levinson |
| 2006/0025788 A1 | 2/2006 | Loshakove et al. |
| 2006/0212066 A1 | 9/2006 | Hamman |
| 2008/0004640 A1 | 1/2008 | Ellingwood |
| 2008/0027482 A1 | 1/2008 | Sekido et al. |
| 2008/0177276 A1 | 7/2008 | Teague et al. |
| 2008/0293996 A1 | 11/2008 | Evans et al. |
| 2009/0005725 A1 | 1/2009 | Shorey |
| 2009/0054841 A1 | 2/2009 | Hamman |
| 2009/0076454 A1 | 3/2009 | Hamman et al. |
| 2009/0093825 A1 | 4/2009 | Logan |
| 2009/0264835 A1 | 10/2009 | Schuermann |
| 2009/0270908 A1 | 10/2009 | Tekulve et al. |
| 2009/0287193 A1 | 11/2009 | Desai et al. |
| 2010/0010533 A1 | 1/2010 | Burke et al. |
| 2010/0010608 A1 | 1/2010 | Tockman et al. |
| 2010/0057053 A1 | 3/2010 | Terashi et al. |
| 2010/0185228 A1 | 7/2010 | Tekulve et al. |
| 2010/0318065 A1 | 12/2010 | Miyata et al. |
| 2010/0331954 A1 | 12/2010 | Sahatjian et al. |
| 2011/0004238 A1 | 1/2011 | Palmer et al. |
| 2011/0066159 A1 | 3/2011 | Teague et al. |
| 2011/0082385 A1 | 4/2011 | Diaz et al. |
| 2011/0130624 A1 | 6/2011 | Hamman et al. |
| 2012/0271336 A1 | 10/2012 | Hamman et al. |
| 2013/0267985 A1 | 10/2013 | Arcia et al. |

FOREIGN PATENT DOCUMENTS

| | | |
|---|---|---|
| JP | 2004167214 | 6/2004 |
| WO | WO 01/70119 A1 | 9/2001 |
| WO | WO 2011/068591 | 6/2011 |

OTHER PUBLICATIONS

USPTO Oct. 17, 2007 Response to Aug. 15, 2007 Nonfinal Office Action from U.S. Appl. No. 11/084,453.
USPTO Feb. 21, 2008 RCE Response to Jan. 10, 2008 Final Office Action from U.S. Appl. No. 11/084,453.
USPTO Jun. 10, 2008 Response to Apr. 22, 2008 Nonfinal Office Action from U.S. Appl. No. 11/084,453.
USPTO Sep. 2, 2008 Final Office Action from U.S. Appl. No. 11/084,453.
USPTO Sep. 22, 2008 RCE Response to Sep. 2, 2008 Final Office Action from U.S. Appl. No. 11/084,453.
USPTO Dec. 9, 2008 Nonfinal Office Action from U.S. Appl. No. 11/084,453.
USPTO Dec. 22, 2008 Response to Dec. 9, 2008 Nonfinal Office Action from U.S. Appl. No. 11/084,453.
USPTO Mar. 16, 2009 Final Office Action from U.S. Appl. No. 11/084,453.
USPTO Mar. 27, 2009 RCE Response to Mar. 16, 2009 Final Office Action from U.S. Appl. No. 11/084,453.
USPTO Jun. 17, 2009 Nonfinal Office Action from U.S. Appl. No. 11/084,453.
USPTO Sep. 17, 2009 Response to Jun. 17, 2009 Nonfinal Office Action from U.S. Appl. No. 11/084,453.
USPTO Jan. 7, 2010 Final Office Action from U.S. Appl. No. 11/084,453.
USPTO Mar. 9, 2010 Appeal Brief Office Action from U.S. Appl. No. 11/084,453.
USPTO Jun. 2, 2010 Notice of Allowance from U.S. Appl. No. 11/084,453.
USPTO Jan. 14, 2011 Nonfinal Office Action from U.S. Appl. No. 12/332,058.
USPTO Apr. 14, 2011 Response to Jan. 14, 2011 Nonfinal Office Action from U.S. Appl. No. 12/332,058.
USPTO Apr. 15, 2011 Nonfinal Office Action from U.S. Application No. 11/18/2008.
Non-Final Office Action in U.S. Appl. No. 11/842,541 mailed on Nov. 9, 2010.

(56) References Cited

OTHER PUBLICATIONS

Response to Non-Final Office Action dated Nov. 9, 2010 in U.S. Appl. No. 11/842,541, filed Feb. 3, 2011.
Final Office Action in U.S. Appl. No. 11/842,541 mailed on Apr. 14, 2011.
Request for Continued Examination and Amendment in U.S. Appl. No. 11/842,541, filed Jul. 14, 2011.
Non-Final Office Action in U.S. Appl. No. 12/273,484 mailed on Apr. 15, 2011.
Response to Non-Final Office Action dated Apr. 15, 2011 in U.S. Appl. No. 12/273,484, filed Jul. 15, 2011.
Response to Non-Final Office Action dated Jan. 14, 2011 in U.S. Appl. No. 12/332,058, filed Apr. 14, 2011.
Final Office Action in U.S. Appl. No. 12/332,058 mailed on Jun. 14, 2011.
R.K. Wolf, M.D., "Anastomotic Defices for Coronary Surgery," May 2004, 7 pages.
Ernesto Tappainer, "New Device for Saphenous Vein-to-Aorta Proximal Anastomosis Without Side-Clamping," Journal of Cardiothoracic Surgery, Apr. 17, 2007, 31 pages.
USPTO Feb. 3, 2011 Response to Non-Final Office Action dated Nov. 9, 2010 in U.S. Appl. No. 11/842,541, filed Feb. 3, 2011.
Apr. 14, 2011 Final Office Action in U.S. Appl. No. 11/842,541 mailed on Apr. 14, 2011.
Response to Non-Final Office Action dated Apr. 15, 2011 in U.S. Appl. No. 12/273,494, filed Jul. 14, 2011.
Final Office Action in U.S. Appl. No. 12/332,508 mailed on Jun. 14, 2011.
Medtronic, "U-Clip™ Anastomotic Device and Spyder® Device," copyright Medtronic, Inc. 2007, http://www.medtronic.com/cardsurgery/products/uclip_spyder.html#, retrieved Oct. 30, 2009, 2 pages.
Novare Surgical, "Enclose® II Anastomosis Assist Device," copyright 2009 Novare Surgical Systems, Inc., http://www.novaresurgical.com/enclose2/enclose2device/, retrieved Oct. 30, 2009, 1 page.
MedGadget, "Heartstring III Proximal Seal System for CABG," Apr. 14, 2008, copyright 2004-2009 Medgadget LLC, http://medgadget.com/archives/2008/04/heartstring_iii-proximal_seal_system_for_cabg.html, retrieved Oct. 30, 2009, 6 pages.
USPTO Nonfinal Office Action dated Aug. 15, 2007 for U.S. Appl. No. 11/084,453, filed Mar. 18, 2005, 8 pages.
USPTO Final Office Action dated Jan. 10, 2008 for U.S. Appl. No. 11/084,453, filed Mar. 18, 2005, 7 pages.
USPTO Nonfinal Office Action dated Apr. 22, 2008 for U.S. Appl. No. 11/084,453, filed Mar. 18, 2005, 9 pages.
U.S. Appl. No. 12/629,656, filed Dec. 2, 2009 entitled "System and Method for Attaching a Vessel in a Vascular Environment," Inventor(s) Baron L. Hamman, et al.
Final Office Action in U.S. Appl. No. 12/273,484 mailed on Oct. 21, 2011.
Request for Continued Examination and Amendment in U.S. Appl. No. 11/332,058, filed Sep. 16, 2011.
Request for Continued Examination and Amendment in U.S. Appl. No. 12/273,484, filed Jan. 23, 2012.
U.S. Appl. No. 13/359,437, filed Jan. 26, 2012, entitled "System and Method for Attaching a Vessel in a Vascular Environment," inventors William E. Cohn et al.
U.S. Appl. No. 13/358,700, filed Jan. 26, 2012, entitled "System and Method for Loading a Graft Vessel on a Vessel Holding Device for Delivery in a Vascular Environment," inventor Kirk S. Honour.
International Preliminary Report on Patentability and Written Opinion issued in PCT Application serial No. PCT/US2010/052253 mailed on Jun. 14, 2012.
Notice of Allowance in U.S. Appl. No, 11/842,541 mailed on Mar. 14, 2013.
Non-Final Office Action in U.S. Appl. No. 12/276,484 mailed on Mar. 29, 2013.
Non-Final Office Action in U.S. Appl. No. 12/629,656 mailed on Jul. 5, 2012.
Response to Non-Final Office Action dated Jul. 5, 2012 in U.S. Appl. No. 12/629,656, filed Oct. 5, 2012.
Final Office Action in U.S. Appl. No. 12/629,656 mailed on Jan. 3, 2013.
Request for Continued Examination and Amendment in U.S. Appl. No. 12/629;656, filed Apr. 3, 2013.
U.S. Appl. No. 13/541,290 entitled "System and Method for Measuring a Vessel in a Vascular Environment," filed on Jul. 3, 2013; inventors Baron L. Hamman et al.
Response to Restriction Requirement in U.S. Appl. No. 13/541,290, filed Jan. 14, 2014.
Japan Patent Office First Notice of Reasons for Refusal in Japanese Patent Application Serial No. JP 2012-542006 mailed on Oct. 17, 2013.
Response to Non-Final Office Action in U.S. Appl. No. 12/273,484, filed Jul. 1, 2013.
Final Office Action in U.S. Appl. No. 12/273,484 mailed on Oct. 11, 2013.
Supplemental Amendment in U.S. Appl. No. 12/629,656, filed May 14, 2013.
Notice of Allowance in U.S. Appl. No. 12/629,656 mailed on May 24, 2013.
Non-Final Office Action in U.S. Appl. No. 13/359,437 mailed on Jul. 18, 2013.
U.S. Appl. No. 13/621,205 entitled "System and Method for Providing an Elongated Coil Guide in a Vascular Environment" inventor(s) Kirk S. Honour et al., filed on Sep. 15, 2012.
Non-Final Office Action in U.S. Appl. No. 13/621,205 mailed on Nov. 15, 2013.
U.S. Appl. No. 13/851,903, filed Mar. 27, 2013 and entitled "System and Method for a Multi-Head Cutter in a Vascular Environment", Inventors, Kirk S. Honour et al.
U.S. Appl. No. 13/851,943, filed Mar. 27, 2013 and entitled "System and Method for a Multi-Head Cutter in a Vascular Environment", Inventors, Kirk S. Honour et al.
Response to Non-Final Office Action dated Jul. 18, 2013 in U.S. Appl. No. 13/359,437, filed Oct. 18, 2013.
Final Office Action in U.S. Appl. No. 13/359,437 mailed on Dec. 10, 2013.
Non-Final Office Action in U.S. Appl. No. 13/358,700 mailed on Nov. 21, 2013.
AF Response to Final Office Action dated Oct. 11, 2013 in U.S. Appl. No. 12/273,484, filed on Dec. 11, 2013.
Notice of Allowance in U.S. Appl. No. 12/273,484 mailed on Dec. 26, 2013.
Non-Final Office Action in U.S. Appl. No. 12/332,058 mailed on Dec. 20, 2013.
Restriction Requirement in U.S. Appl. No. 13/541,290 mailed on Jan. 6, 2014.

* cited by examiner

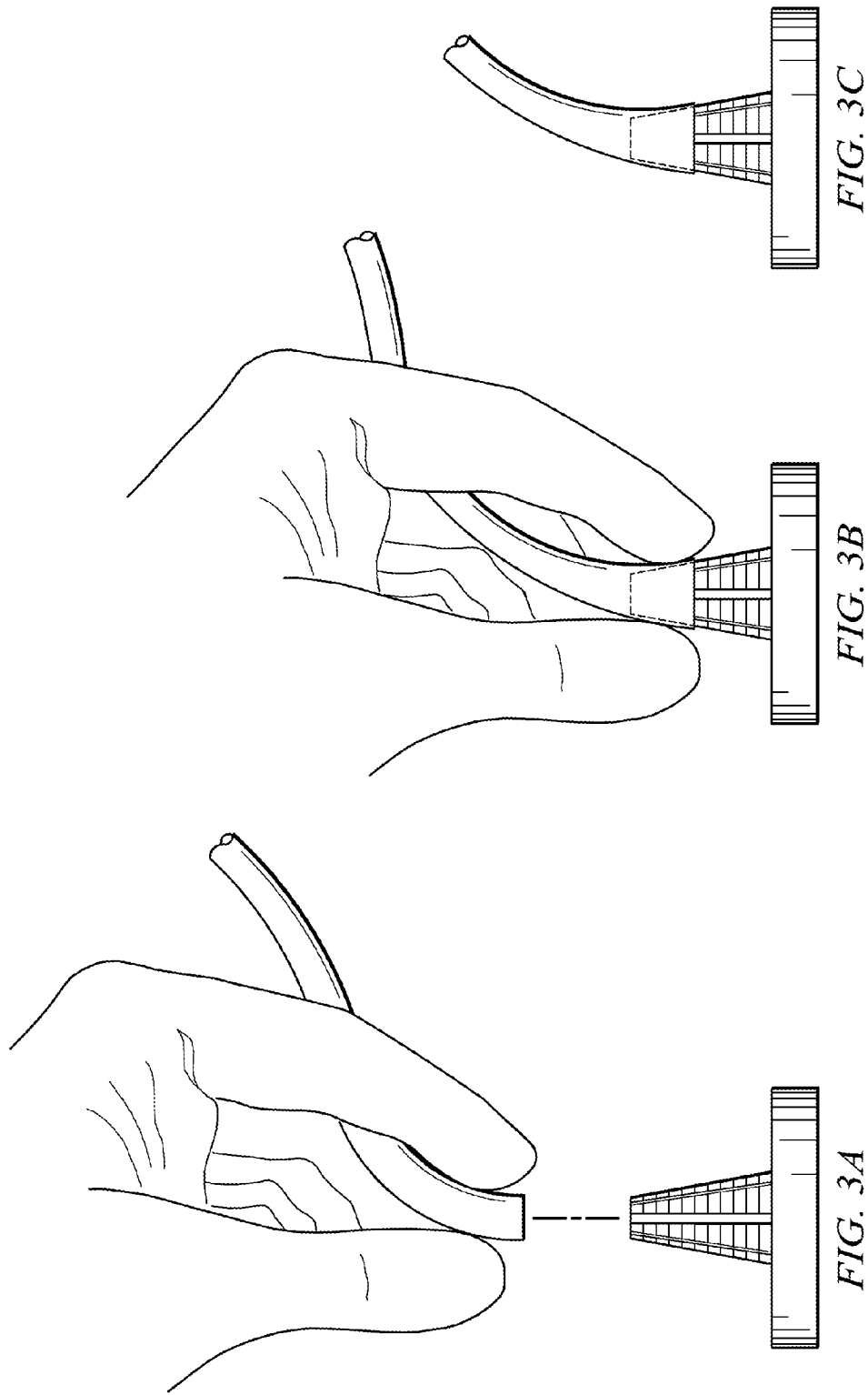

SYSTEM AND METHOD FOR ATTACHING A VEIN, AN ARTERY, OR A TUBE IN A VASCULAR ENVIRONMENT

This application is a divisional and claims the benefit of priority under 35 U.S.C. §120 and §121 of U.S. application Ser. No. 11/084,453, filed Mar. 18, 2005, now issued as U.S. Pat. No. 7,763,037. The preceding application is expressly incorporated herein by reference in its entirety.

TECHNICAL FIELD OF THE INVENTION

This invention relates in general to the field of cardiac and vascular surgery and, more particularly, to a process, a system, and a method for attaching a vein, an artery, or a tube in a vascular environment.

BACKGROUND OF THE INVENTION

The treatment of vascular diseases has grown exponentially in terms of sophistication and diversity. In particular, coronary artery bypass graft (CABG) surgery has become routine in most cardio-thoracic practices. Its popularity is due, in part, to its tremendous success rate and its ability to offer extraordinary benefits to a patient.

CABG surgery restores blood flow to heart tissue that has been deprived of blood because of coronary artery disease. During bypass surgery, a new graft vessel, which will subsequently carry oxygenated blood around the blockage in a coronary artery, is surgically removed from another location in the body. The harvested graft vessel is a healthy artery or vein taken from the leg, arm, or chest. The vessel is then transferred to the outside of the heart. Concisely stated: the graft vessel supplies oxygenated blood to the part of the heart that needs it.

CABG procedures substantially improve problematic conditions/symptoms in more than 90% of patients who undergo the treatment. The procedure also helps to prolong lives for people having either left main coronary disease or blockages in several of the major vessels (especially in cases where the pumping action of the heart is also being reduced or restricted).

One issue associated with any bypass operation relates to flexibility. An attending physician must often complete a number of sophisticated tasks during a given procedure. Therefore, optimizing or simplifying any of these steps may yield a significant reduction in work for a surgeon. In addition, there is a significant amount of estimating or guesswork that normally transpires during a given bypass operation. For example, approximations may be made for cutting a hole in the aortic wall. Once a vein is harvested for a bypass procedure, a physician can only guess as to its size. This may result in making holes in the aortic wall that are simply incorrect. Moreover, many bypass instruments are cumbersome, difficult to manipulate, potentially harmful to patients, and clumsy or awkward in many situations. Their deficiencies create a significant burden on the physician, who is already being taxed by a number of arduous tasks. In addition, many current devices are unacceptable because they violate the interior of the aorta, which (in turn) can cause trauma and inflammation issues.

Accordingly, the ability to provide an effective medical instrument that properly accounts for the aforementioned problems presents a significant challenge for component manufactures, system designers, and physicians alike.

SUMMARY OF THE INVENTION

From the foregoing, it may be appreciated by those skilled in the art that a need has arisen for an improved bypass instrument for achieving superior control, management, and performance during a bypass procedure. In accordance with an embodiment of the present invention, a device, a system, and a method for enhancing a bypass operation are provided that includes a flexible, highly precise, easy-to-use device, which substantially eliminates or greatly reduces disadvantages and problems associated with conventional bypass equipment and instruments.

According to an embodiment of the present invention, a device for assisting in a vascular procedure is provided that includes a handle and one or more legs that are operable to move in response to a force being applied to the handle. The legs are operable to extend and to contract in order to manipulate a conduit. In a more particular embodiment, the device can be used in conjunction with a stand operable to receive the conduit such that the conduit can be removed from the stand by the device. The stand may include one or more graduations that indicate the size of the conduit once it is positioned on the stand. In yet another embodiment of the present invention the device can be used with a cradle operable to hold the stand such that the conduit can be removed by the device. An actuator may also cooperate with the device in order to facilitate one or more operations of the device.

Certain embodiments of the present invention may provide a number of technical advantages. For example, according to one embodiment of the present invention, an architecture and a process are provided that offer a flexible system, which can easily accommodate a vein of any size. The present system can include a simple loading procedure that offers exceptional flexibility and adaptability for a physician. In addition, the present invention offers increased accuracy for a surgeon who must make a precise incision in the aortic wall. In one embodiment, graduations may be provided on a stand (which stabilizes the vein) in order to clearly elucidate the exact size of the harvested vein and, therefore, dictate the size of the hole to be made in the aortic wall. In addition, the procedure associated with the present invention is minimally invasive, whereby clamping of the aorta (which can be problematic) is no longer necessary.

The present invention also offers a device that avoids any injury or damage to the harvested vein. The integrity of the vein is maintained during the tendered process, as the physician can suitably position and then transport the vein in a safe and reliable manner. Additionally, any violation of the aorta is effectively avoided in the operation of the present invention. Moreover, the present invention may involve suturing operations, which can be beneficial in a number of respects. For example, suturing may be preferred because it offers minimal stress to a somewhat fluid system, which responds negatively to sheer, torque, and other external forces. Thus, flexibility is incorporated into the device, as it readily allows for suturing and clipping operations to be performed. Note that suturing operations offer a consistent and an effective protocol for a surgeon, who is accustomed to performing such familiar tasks. Note also that the design of the present invention facilitates the suturing process, as outlined below. Additional advantages are described herein with reference to corresponding FIGURES.

Certain embodiments of the present invention may enjoy some, all, or none of these advantages. Other technical advantages may be readily apparent to one skilled in the art from the following figures, description, and claims.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which:

FIGS. 3A-3I are simplified schematic diagrams of an example operation that implicates the device;

DETAILED DESCRIPTION OF THE INVENTION

Figure 1:
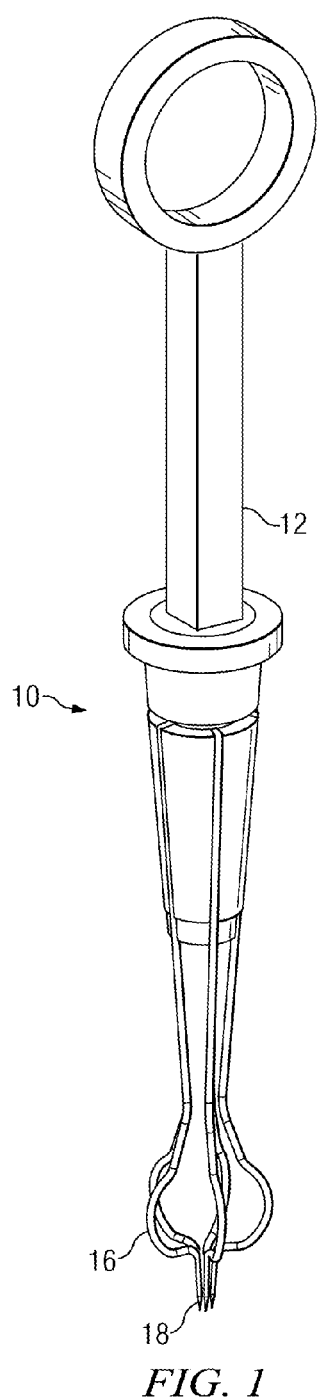
FIG. 1 is a simplified schematic diagram illustrating a device to be used in a bypass procedure in accordance with one embodiment of the present invention.

FIG. 1 is a simplified schematic diagram of a device 10, which may be used during a bypass operation. Device may include a handle 12 and one or more legs 16, which include one or more tips 18. By pushing or by pulling on handle 12, one or more of legs 16 may extend, separate, and/or open in order to grasp or to initiate contact with any suitable object.

Tips 18, which are sharp and which are provided on each of legs 16, may be used to pierce a vein being used in a given bypass procedure. Tips 18 allow for a precise removal of the vein from a loading structure (e.g. a stand or a base), which is described in greater detail below with reference to FIGS. 2A-C. In particular, legs 16 may be controlled such that they are operable to lift a vein directly from the loading structure.

Legs 16 may be constructed of any suitable material (e.g. steel, titanium, plastic, etc.) and be provided in any appropriate configuration or orientation. In one embodiment, five legs 16 are provided and configured such that when handle 12 is manipulated, legs 16 simply open and close a certain length or range. Alternatively, device 10 may include any number of legs 16 such that a vein can be properly maneuvered or manipulated by device 10.

One or more settings may be provided to device 10 such that by controlling handle 12, legs 16 respond by extending a certain distance (e.g. 2 millimeters). As is illustrated in FIG. 1, legs 16 of device 10 are constructed with a particular curvature such that they can navigate around a loading structure, while accurately pricking or retrieving a vein while it is on the loading structure. The leg curvature and design allows for an optimal positioning of the vessel at the aortonomy, as well as offering clearance for suturing of the vein to the aorta. The clearance that is afforded by device 10 is critical, as it provides a platform for accommodating a bulbous patent atrium to receive an effective suturing operation. Alternatively, such a curvature and/or design may be changed or modified considerably in order to accommodate particular arrangements or configurations. The illustrated example of FIG. 1 can be altered considerably without departing from the broad teachings of the present invention.

Before proceeding further, for purposes of teaching and discussion, it is useful to provide some overview as to the way in which the following invention operates. The following foundational information may be viewed as a basis from which the present invention may be properly explained. Such information is offered earnestly for purposes of explanation only and, accordingly, should not be construed in any way to limit the broad scope of the present invention and its potential applications.

Coronary artery bypass graft (CABG) surgery is one of the most complex surgeries a patient can undergo. The procedure typically requires a few hours to complete, universally involves multiple steps, and routinely involves different techniques (e.g. on-pump vs. off-pump bypass protocols). However, regardless of the steps involved or the different techniques being used, at the end of the procedure, the goal is the same: to bypass blockages in the coronary arteries and to restore healthy blood flow to the heart.

Before the actual placement of bypass grafts begins, the patient is prepped for the procedure, chest access is gained, and medications are administered. When these steps are complete, the surgeon or his assistant begins the process of retrieving the vessels which will be used to create the grafts and, thereby, bypass the blocked coronary arteries.

Choosing the proper graft vessel (which can be any number of sizes) is a critical part of the CABG procedure and the surgeon has several choices in making this selection. For example, the internal mammary artery (IMA) and the surrounding tissue can be retrieved from the chest wall and used as a bypass vessel. Once the IMA is isolated, it is typically left attached to the subclavian artery and then connected to the target artery. Alternatively, the IMA can be removed from the subclavian artery and attached to the aorta and a coronary artery and becomes what is commonly called a free graft.

Other veins to be used could include the saphenous vein in the leg. Following retrieval, the leg wound is closed and the chest is opened for surgery. The leg wound is then closed and the patient's leg is wrapped. Still other operations could include the radial artery, which lies deep within the forearm. Some surgeons feel the radial artery is the second arterial graft of choice (next to the internal mammary arteries). Hence, as highlighted by the examples above, a surgeon may encounter different types of veins: all of which will have their own particular size.

Once the surgeon has determined the proper location on the coronary artery to place the distal end of the bypass graft, the following steps are taken to make the connection: 1) the coronary artery (target vessel) is cut at a point away from the blockage; 2) the bypass vessel is connected to the side of the target vessel; 3) a hole is placed in aorta; 4) the bypass vessel is connected to the aorta (the proximal attachment); 5) the process is repeated for each of the remaining grafts; and 6) flow is checked to assure that the grafts supply adequate blood to the heart.

If the procedure has been done on-pump, after the grafts are placed, the physician will restart the heart, remove the patient from the bypass machine, recheck the grafts for flow, and then remove the bypass tubes. When this has been completed, or if the procedure was done off-pump, the surgeon will drain the remaining fluid from the chest cavity and move the patient to intensive care for monitoring during the initial recovery.

If a surgeon stops the heart for bypass surgery, cardiopulmonary bypass (CPB) is used. This is known as an on-pump procedure. CPB requires the heart to be arrested and filled with a solution called cardioplegia to keep it still. During this time and throughout the procedure, a pump takes over the function of the heart (cardio) and lungs (pulmonary).

To accomplish CPB, a cannulating tube is inserted into the aorta to carry oxygenated blood from the bypass machine to the aorta for circulation to the rest of the body. Other tubes are inserted into the major veins that bring blood back to the right atrium of the heart. The blood from these major veins goes to the machine for oxygenation and temperature adjustment, instead of going to the heart. The oxygenated blood is then returned to the body through the aortic tube.

During cardiopulmonary bypass, aortic clamps are also used to restrict blood flow to the area where grafts will be placed. These clamps will remain closed on the aorta until the grafts are in place. Clampless bypass surgery was developed to further reduce the complications associated with manipulation of the aorta during bypass procedures. Just as in off-pump bypass, the heart is not stopped, tubes are not placed in the aorta, and cardioplegia is not used to keep the heart still. The heart continues to beat and supply the body with oxygenated blood throughout the procedure.

Following placement of the grafts, the patient is ready to come off bypass. At this time, the blood is rewarmed (if necessary), the lungs are inflated, and respiration is restored. The tubes are then removed and a slow transition takes place to bring the blood back into the body and begin circulating on its own. The patient is technically off-pump when the heart takes over its normal function.

Off-pump surgery differs from on-pump surgery in that the heart is not stopped, no tubes are placed in the aorta, and cardioplegia is not used to keep the heart still. During off-pump procedures, the heart continues to beat and to supply the body with oxygenated blood. Off-pump techniques were developed because of the belief that working on-pump puts patients at a higher risk of experiencing certain complications. With the use of off-pump techniques, surgeons provide the same graft results through a less invasive, although technically more complicated, procedure.

The most significant difference in the clampless technique is the elimination of the clamps used to squeeze the aorta to isolate an area of it from blood flow so it can be sewn to. This is enabled through the use of mechanical connectors, which provide a graft connection much like sutures, but can be used on the aorta without manipulation or clamping.

It is important to understand that both on-pump and off-pump bypass procedures offer advantages and disadvantages. While one may seek to reduce the risk of cardiopulmonary bypass, the other avoids the technical challenge of placing bypass grafts on a beating heart. Ultimately, both share the same goal, to effectively utilize bypass grafts to restore blood flow to the heart.

Having reviewed the basic tenets of bypass operations, it should be appreciated that, as a general proposition, heart surgery is invasive and, therefore, presents a number of risks. For example, during a cardiopulmonary bypass, a machine is used to assume the functions of the heart and lungs during the surgery, as discussed above. Other scenarios involve various permutations of using one or more machines to perform normal bodily functions (e.g. renal functions, lung functions, etc.) for the patient. These machines create torque and sheer issues, as there are a number of Bernoulli forces at work. This creates a significant amount of inflammation, which can be detrimental for the patient.

Many of the current processes for performing bypasses involve invading the blood stream and disrupting a system, which is highly fluid in nature. Note that many organ failures can be attributed to either an inflammation or a blockage. Thus, extreme caution should be taken when working in any area of a patient, which may trigger these complications.

In addition, existing devices that are used in current bypass operations can be difficult to control, as the surgeon must have extraordinary dexterity in manipulating the components. In other scenarios, devices may simply fail to accomplish the objective for which the devices are intended. Other devices may offer benefits associated with ease of use; but these devices are generally flawed because they often improperly violate the inside of the aorta. It should be noted that one ancillary objective in the context of the bypass procedure is to connect the vein to the aorta without touching the inside of the aorta. Contact with the aorta should be avoided because plaque or any other (potentially friable) detrimental element can flake off and become dislodged in other anatomical locations.

Other inadequate systems require the vein to be everted and, therefore, to have two layers of vein at the aorta-vein anastomosis site. The surgeon can correct this after deployment, but most surgeons are averse to manipulating the anastomosis once it has been created. Strangely, many surgeons will actually accept the poor anastomosis (with the everted vein) because its external appearance is acceptable.

Other systems employ the use of an upside-down umbrella that can be rolled up, inserted in a plastic tube, and injected into the aorta (through an aortic hole). When it is unfurled, it provides a relatively bloodless area for manual aorta-vein sutures anastomosis. However, one issue associated with such an arrangement is that it is inside of the aorta: an aorta that still has blood flowing in it. This allows for a clampless anastomosis, but such a configuration still creates a lot of turbulence, which can stress the system and yield undesired transcranial Doppler signals.

Still another problem associated with current bypass processes and systems relates to loading. The vein should be properly stabilized before it is attached to the aortic wall. Veins are inherently supple and floppy. Thus, the vein can flail about while it is being transported or positioned in its designated location. Bypass arrangements that employ the use of the everted umbrella structure identified above suffer terribly in the context of loading issues. Such an arrangement is not ideal in terms of prepositioning and, moreover, is somewhat awkward to manage.

Device 10 overcomes the aforementioned deficiencies in providing an optimal solution for a physician who is relegated the difficult task of performing a bypass procedure. Device 10 is intuitive in that it includes a simple loading procedure that offers exceptional flexibility and adaptability for a physician. In addition, device 10 offers enhanced accuracy for a surgeon who must make a precise incision in the aortic wall. No longer would a surgeon have to guess or to estimate the size of the hole in the aortic wall. A number of graduations (discussed in greater detail below) are provided on stand 20 in order to illustrate the exact size of the harvested vein and, therefore, dictate the size of the opening in the aortic wall. Additionally, such a procedure is minimally invasive because clamping of the aorta (which can be problematic) is no longer necessary.

One advantage of device 10 is its adjustability. Device 10 is designed to accommodate a broad range of sizes of vessels (e.g. 2 to 8 mm diameter) which can be positioned and readily sized on stand 20. As identified herein, sizing on this proverbial "vessel holder" also helps to identify the size of punch or cutter required for the anastomosis for each individual vessel. These features and attributes stand in stark contrast to other devices, which are not only limited in sizing and flexibility, but that also fail to accommodate the use of radial arteries.

Most surgeons would prefer a device to be unencumbered by size restrictions and, further, to cooperate with beveled cuts. Beveled cuts are generally optimal for bypass procedures because a beveled edge provides a greater margin of safety (i.e. a surgeon can be successful in his suturing procedure while making a number of sewing mistakes). The beveled edge creates a larger circumference such that technical inadequacies have a minimal impact on the surface of the aorta. Note that many surgeons generally prefer sewing, as opposed to stents (which generally comprise NITINOL (Nickel Titanium Naval Ordnance Laboratory)) or semiautomatic clips (which are constructed of stainless steel or NITINOL). While not automated, suturing does represent a safe, reliable, and familiar process for the tending physician.

Figure 2A:
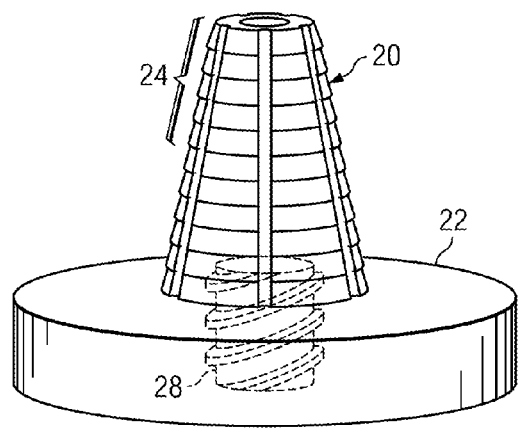
FIGS. 2A-2C are simplified schematic diagrams of a stand, which may be used in conjunction with the device of FIG. 1.
Figure 2B:
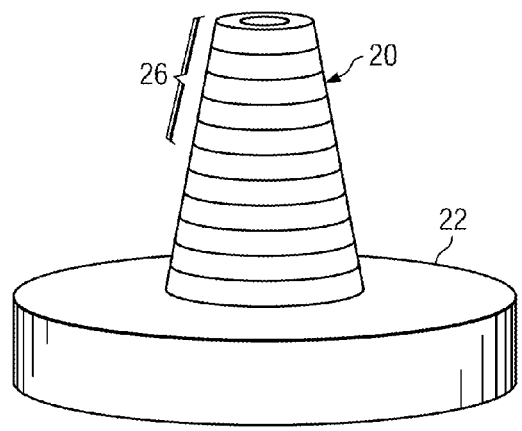
Figure 2C:
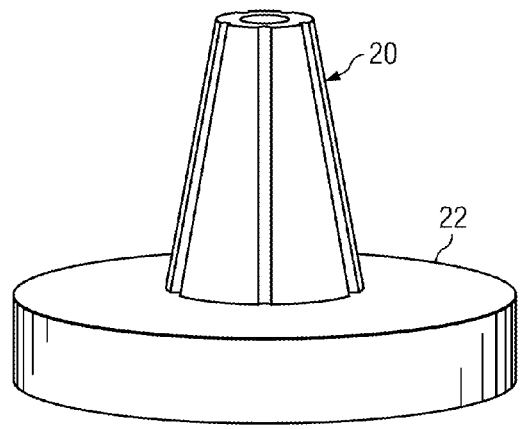

FIGS. 2A-2C are simplified schematic diagrams of a stand 20, which may be used in conjunction with device 10 of FIG. 1. Stand 20 may be constructed such that it is of a shape which accounts for a generic range of vein diameters. Stand 20 may include a suitable base 22. An optional screw mechanism 28 can also be provided such that various sizes of stands or bases may be interchanged. Base 22 should be relatively heavy such that it can fully support stand 20 and offer stability for the physician, who is performing the bypass procedure. Hence, base 22 could be constructed of a heavy metal element, or a somewhat weighty polymer.

FIG. 2A illustrates an example embodiment of stand 20 that is provided with one or more grooves 24 having a particular depth (e.g. 0.35 mm) that is conducive to the loading and unloading operations as described herein. Hence, grooves 24 offer a certain degree of friction for maintaining the position of the vein. Stand 20 may also be used as a guide for device 10 once the vessel is prepositioned.

Stand 20 may be constructed of a somewhat durable material (e.g. a polymer, silicon, rubber, plastic, etc.) to allow tips 18 of device 10 to penetrate stand 20. Stand 20 could comprise a soft and pliable material that is operable to facilitate the operations as described herein. Thus, stand 20 may be used to stabilize the vein, while allowing device 10 to pierce the sides of stand 20 after the vein has been initially stabbed. This could focus the surgeon's attention on piercing the vein, which is of utmost importance, and could facilitate the delicate piercing process. Moreover, such a construction could alleviate problems associated with the damaging the harvested vein.

FIG. 2B represents another embodiment of stand 20 in which stand 20 is provided with one or more ring-shaped grooves 26. Such grooves 26 may be of any requisite depth, size, and shape, and accordingly can be designed based on particular needs. FIG. 2C is yet another example embodiment of stand 20 in which no grooves are provided thereon. Note that a lubricant may be used on any of the embodiments of stand 20 such that placement and removal of the vein is assisted. This may be particularly critical in the embodiment of FIG. 2C.

FIGS. 3A-I are simplified schematic diagrams illustrating how stand 20 can be used by a surgeon to hold/secure the vessel and, further, to size the aortonomy, as described below. Hence, in FIG. 3A a vein may be properly mounted on stand 20. This is a relatively easy step in the process. As illustrated, stand 20 may include one or more graduations (e.g. in millimeters or inches) to assist the surgeon in his vein sizing endeavors. Using the graduations, a surgeon can readily see the exact diameter of the vein, which was harvested. This offers a virtual measuring stick that is incredibly accurate and easy to use for the surgeon.

Note that a physician generally does not have any idea about the size of the vein that was harvested. The vein may be small (e.g. 2 millimeters in diameter) or it could be quite large (e.g. 8-9 millimeters in diameter). The vascular stand 20 provides a number of clear numeric designations such that a physician can easily see the diameter of the vein. Thus, graduations avoid the guesswork associated with approximating the size of the vein. This informs the surgeon of the size of the hole that will be cut in the aorta in a subsequent step of the operation.

FIG. 3B illustrates how the vein is loaded onto stand 20. Note that stand 20 does provide a point of stability for the surgeon. As is evident, stand 20 provides for an easy positioning of the vessel, whereby the clumsiness associated with simultaneously dealing with a vein and an instrument is substantially avoided.

FIG. 3C illustrates a successful loading of the vein such that it is ready to be retrieved by device 10. FIG. 3D illustrates how device 10 may be positioned over stand 20 before attempting to remove the vein. At this point, legs 16 have been protracted or spread out as a result of a manipulation of handle 12. FIG. 3E illustrates device 10 just before engaging the vein. Note that tips 18 may be used as a reference point in order to accurately gauge how far legs 16 should be extended in this instance.

Figure 3F:
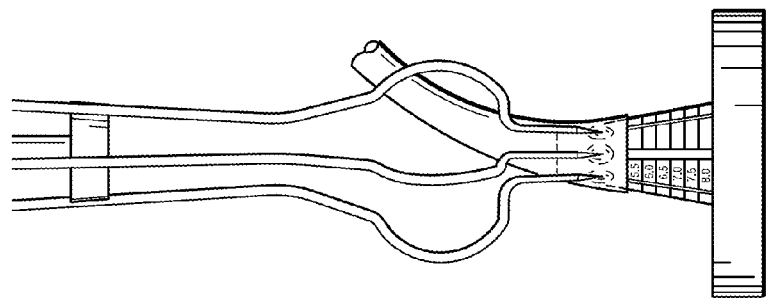
Figure 3E:
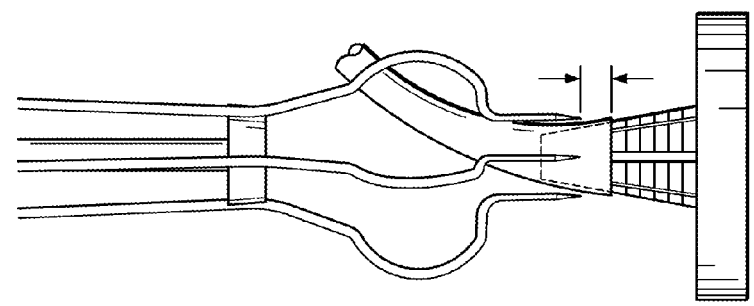
Figure 3D:
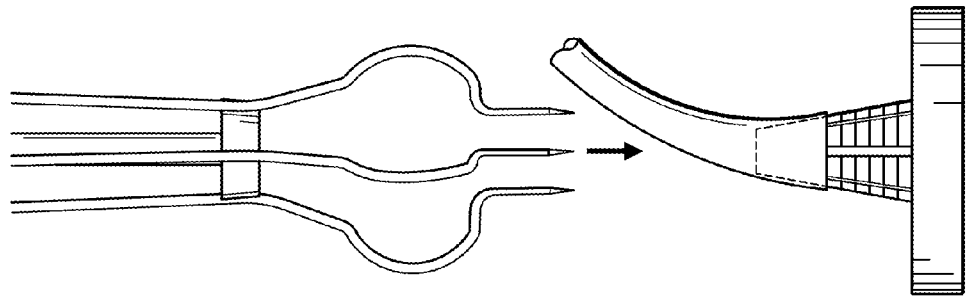

FIG. 3F illustrates the positioning of legs 16 before the vessel is pierced. As is illustrated, the geometry of stand 20 allows for a precise coupling of the anastomotic vessel with device 10. Once the vessel is punctured near the end of the desired proximal end, the vessel can slide (manually) up the shafts of tips 18 to the geometric stop at the first bend. This may reflect a desirable configuration of the aorta-vessel anastomosis. By loading the harvested vessel into the predefined ('final') aorta-vessel proximal configuration, a surgeon can obviate further manipulation later in the anastomosis creation. Note that the identified stop is optional, as device 10 can be designed without such a feature.

FIG. 3F illustrates how one or more graduations may be provided on stand 20. These demarcations are useful to a surgeon who will subsequently cut a hole in the aorta. Hence, the graduations of stand 20 can clearly show the surgeon the size of the vein and, thus, dictate the exact size of the hole to be cut.

Figure 3I:
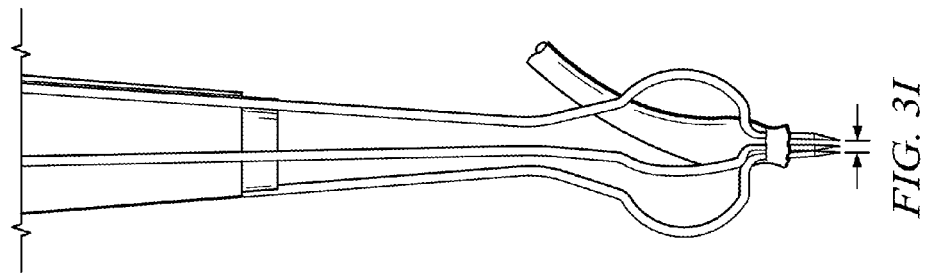
Figure 3H:
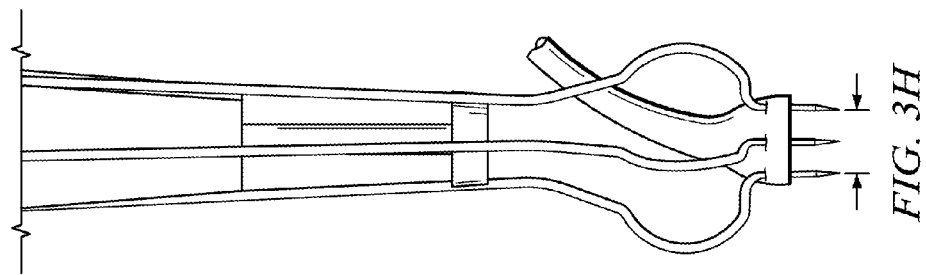
Figure 3G:
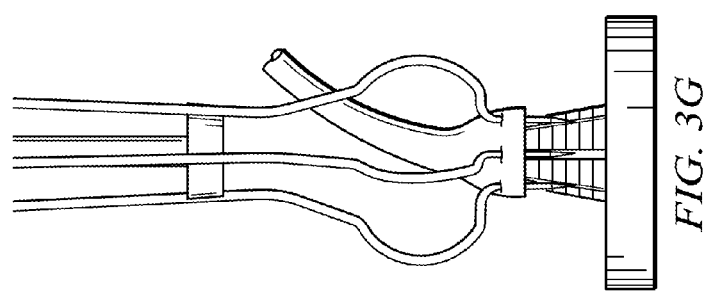

FIG. 3G illustrates how the vein is pierced in order to grasp the vein. As identified above, device 10 may include one or more settings that can automatically extend legs 16 to a specific length. In this example implementation, handle 12 is depressed a certain force in order to position legs 16 such that they are below the vein. Now the vein can be removed from stand 20, which is no longer necessary. Note that stand 20 performs the function of stabilizing the vein, which will be used in the bypass. Stand 20 provides steadiness and control for the physician during the bypass procedure.

FIG. 3H illustrates the vein without stand 20. Note that in order to fit device 10 into the aortonomy, legs 16 need to be relatively small such that they can be fitted into the hole without being ensnared by peripheral elements. As can be appreciated, tips 18 must be sharp enough to pierce the vein, but not necessarily so sharp that they snag/cut everything in their path. For example, tips 18 could be just larger than a standard needle, while still strong enough to easily pierce the vein and interface with stand 20.

FIG. 3I illustrates a contraction of legs 16 such that the vein is now ready to be deployed into the aortic region. This contraction can be effected by a simple manipulation of handle 12. Note that the harvested vein has not been injured or damaged by the foregoing operations: nor has the aorta been violated. The integrity of this vein has been maintained, as the physician can suitably position the vein in a safe and reliable manner at the targeted site.

Figure 4A:
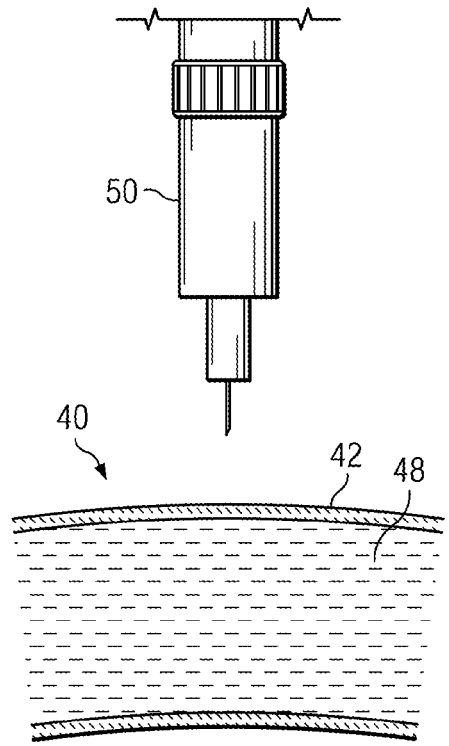
FIGS. 4A-E are simplified schematic diagrams of another example operation that implicates the device.
Figure 4B:
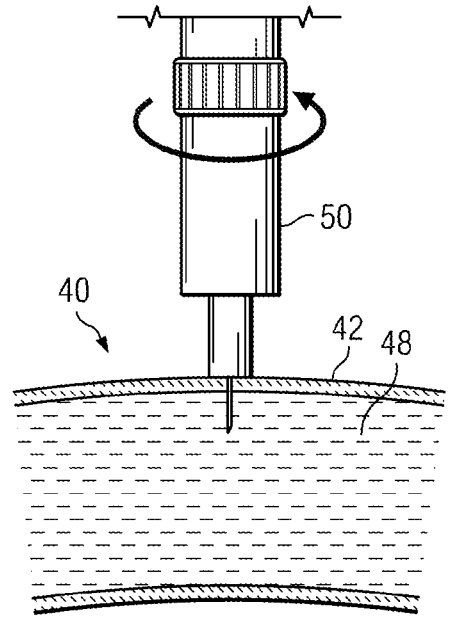
Figure 4C:
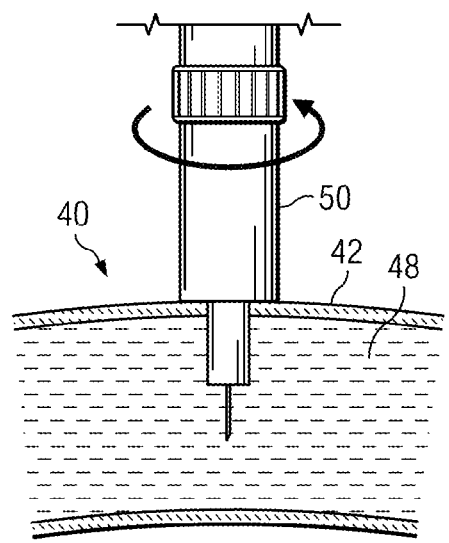

FIGS. 4A-C illustrate how a hole may be cut in an aortic wall 40. FIG. 4A includes a cutter 50, which may be used to make a small incision into the aorta. FIG. 4A also illustrates blood flow 48, as well as an initial aortic layer 42, which is penetrated by cutter 50. The aortic cutter 50 is used to make a uniform hole in the aorta for attaching the vein bypass graft.

Figure 4D:
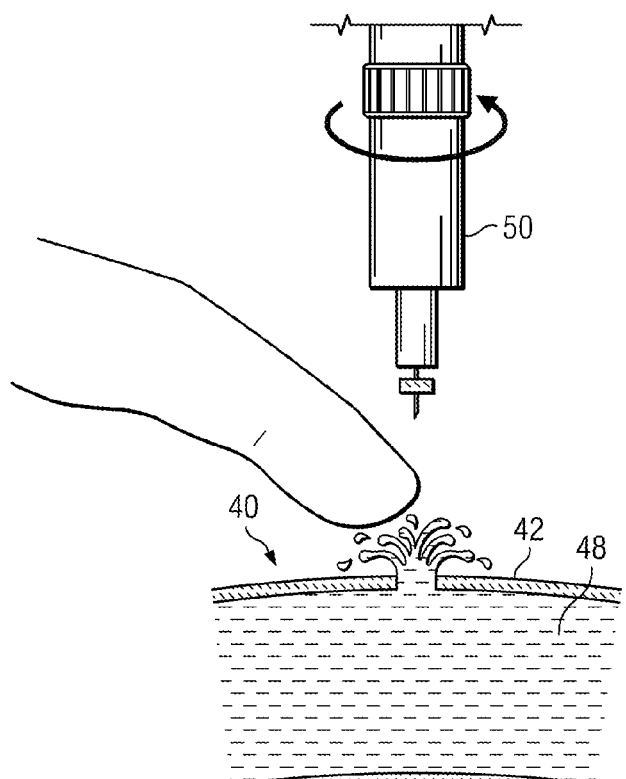
Figure 4E:
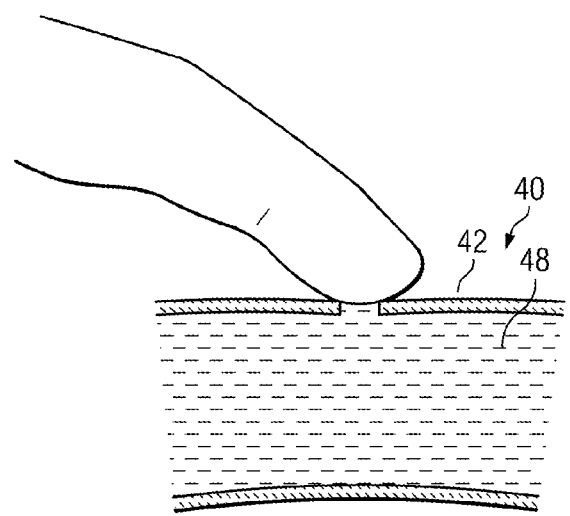

FIG. 4B illustrates cutter 50 being engaged, whereby layer 42 is pierced. FIG. 4C illustrates cutter 50 being suitably positioned within aortic wall 40 just before the hole is actually cut. FIG. 4D illustrates the hole that was created and the resulting blood flow. Cutter 50 may be automatic or mechanical, as its rotation can produce a uniform incision in either case. Because of the blood flow, the surgeon can simply put his finger over the hole prior to plugging the hole with the vein, as is illustrated by FIG. 4E.

Figure 5A:
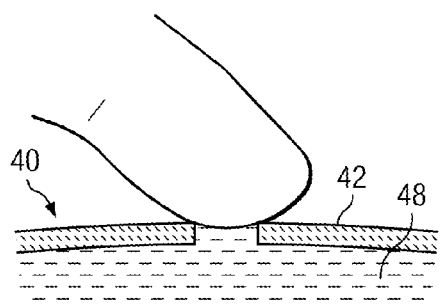
FIGS. 5A-E are simplified schematic diagrams of yet another example operation that implicates the device.
Figure 5B:
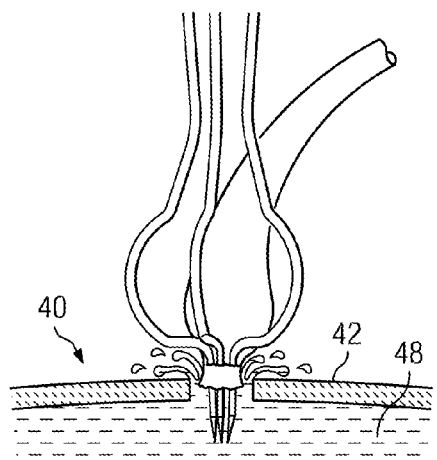
Figure 5C:
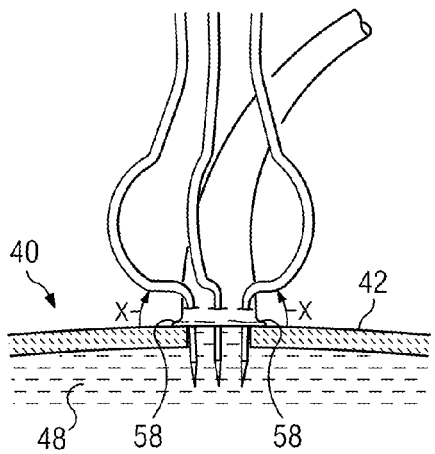

FIGS. 5A through 5E illustrate a transfer operation in which the vein is used to fill the void in the aortic wall. This process involves the proximal attachment, whereas the distal attachment involves a separate procedure. FIG. 5A illustrates how the physician has stopped the blood flow emanating from a hole that was cut. FIG. 5B shows how the hole is plugged with device 10, which now includes the loaded vein. At this stage, legs 16 are somewhat close together and the vein is compressed. Handle 12 can then be pulled or pushed such that legs 16 are somewhat extended and the vein is, thereby, expanded, as is shown in FIG. 5C.

Note that there is some pressure in the vein such that, once suitably positioned, the vein will inflate to capacity. FIG. 5C further illustrates the design consideration that can be given to legs 16. An angle 'X' is created between aortic wall 42 and legs 16. This enables a lip 58 of the vein to be produced, which can further enable the suturing process.

It should also be noted that current inadequate bypass instruments may require a deployment of feet or skids for the purpose of prepositioning the vein at the right level in the aortic hole. The geometry of device 10 serves that purpose without deploying and retracting a set of feet. Hence, device 10 is much simpler and more effective in its design, which minimizes manipulation by the surgeon in placing and retracting the bypass vessel.

Figure 5D:
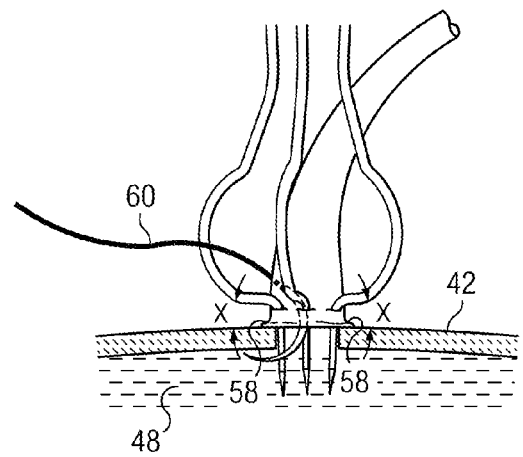

FIG. 5D illustrates the seal that is formed, whereby the vein is taut and ready to be sutured to the aorta. FIG. 5D illustrates a first suture 60 being positioned around the vein. Alternatively, a clip or some other mechanism may be used to join these two interfaces. (Note that an alternative to suturing is provided in FIGS. 7A-D and described in greater detail below.) Sutures may be ideal because they are benign and because they offer a simple protocol for the surgeon.

Figure 5E:
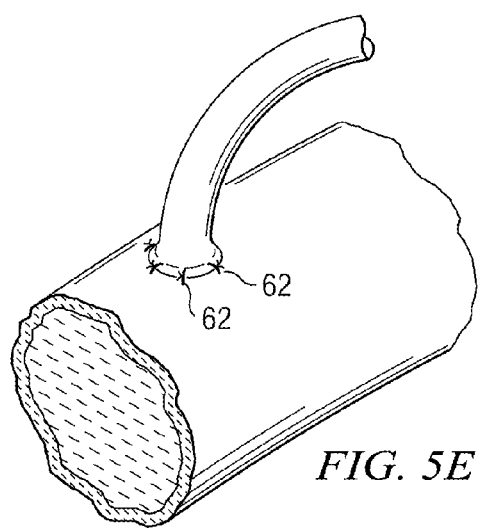

FIG. 5E illustrates a series of sutures 62 having been properly placed around the bypass vein. The suturing operation was assisted by the design of legs 16, whereby such a fastening procedure provides a reliable means for securing the vein to the aortic wall. Utilizing such a suturing approach achieves some level of comfort for the tending surgeon, as suturing represents a customary method of accomplishing such an attachment.

Hence, the operation of device 10 may require a surgeon to apply sutures to make the aorta-vessel connection. Note that sutured anastomoses have performed satisfactory such that departing from such an adequate protocol is unnecessary. Device 10 would afford the ability to apply a continuous prolene suture or an interrupted suture at the anastomosis. Interrupted sutures have performed somewhat better and are particularly important in small vascular anastomosis. Device 10 may also allow the surgeon to apply custom clips at original angles to account for the vagaries of the human/biological vessel.

Figure 6A:
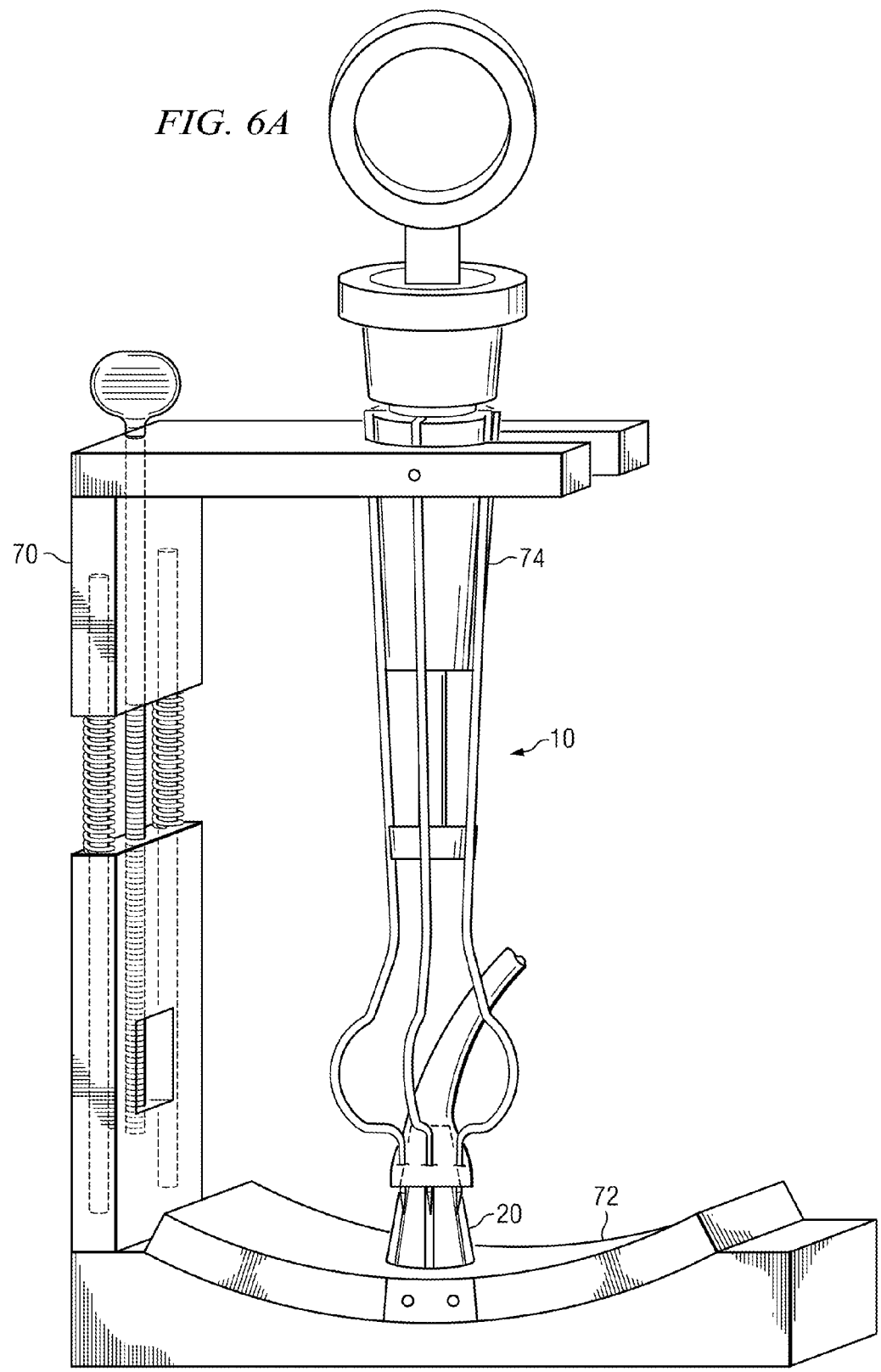
FIGS. 6A-B are simplified schematic diagrams of a cradle configuration that may be used in conjunction with the device.
Figure 6B:
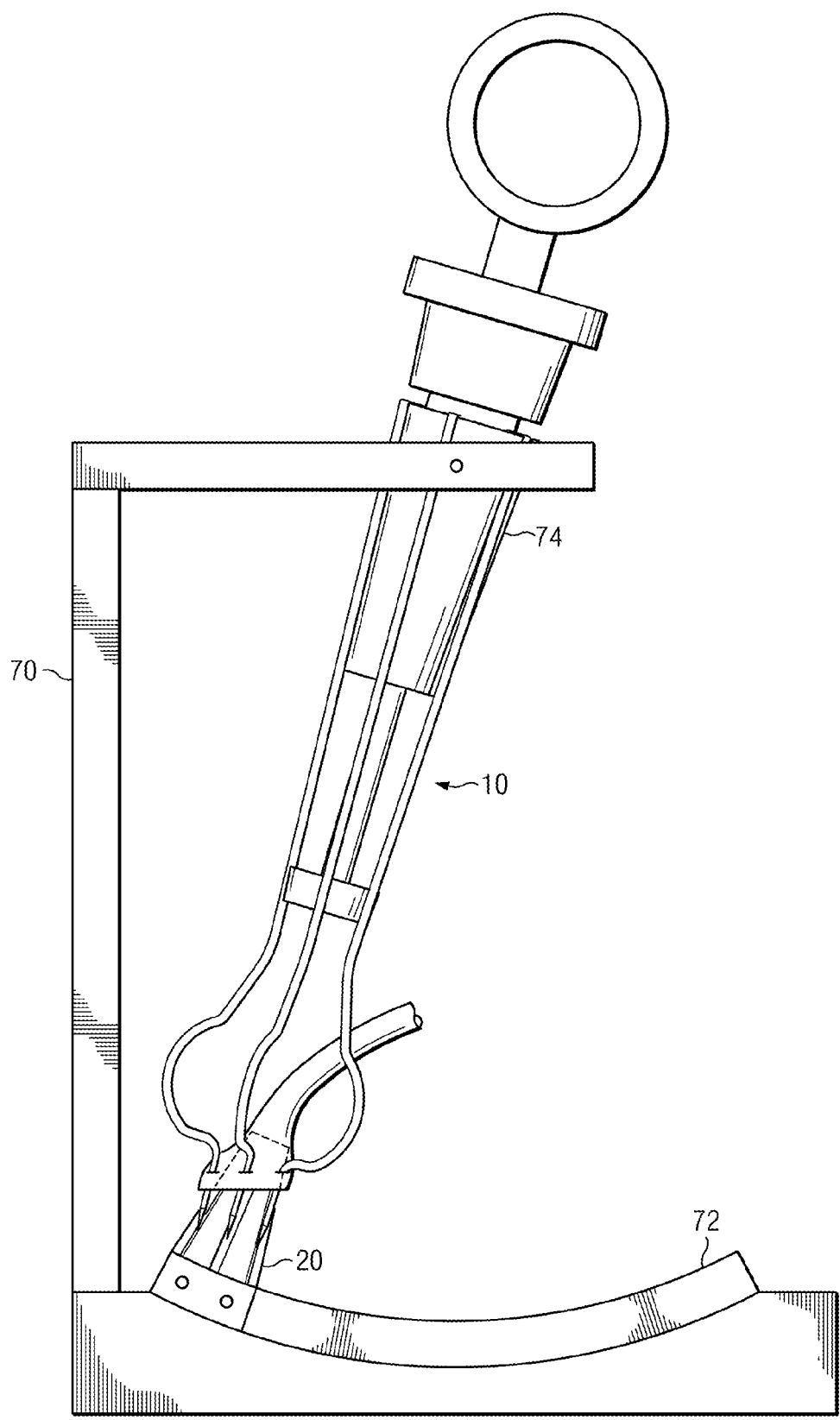

FIGS. 6A-B illustrate a potential ancillary component of the present invention. FIG. 6A illustrates a clamp 70 and a cradle 72, which allows for movement of stand 20 in order to allow device 10 to pick up the vein after it has been successfully loaded. Clamp 70 can be a simple component, such as a test-tube stand and/or a C-clamp device, that includes one or more graduations and that can be used to stabilize device 10. Cradle 72 may be provided to produce lateral movement, whereby device 10 is positioned immediately above stand 20, as is illustrated.

An actuator 74 is also provided for device 10, which can be used with or without cradle 72. Actuator 74 may be provided to automate one or more of the operations as described herein in this document. This could include operations that relate to piercing the vein, extending legs 16, or driving fastening mechanisms into the aortic wall, as described below with reference to FIGS. 7A-D. Actuator 74 may also be used to rotate device 10. For example, the rotation of actuator 74 in FIG. 6B may facilitate removing a vein having a beveled or a cobra edge.

The embodiment of FIG. 6A also includes an optional securing clip (i.e. a loading dock type mechanism) that can receive actuator 74. Hence, actuator 74 could snap into place and be held securely by clamp 70. Clamp 70 could be adjustable, which could allow device 10 to be moved up and down. Such an adjustability feature may be facilitated by a guide rod that could allow for a precise manipulation of device 10 such that it can lift a harvested vein from stand 20 in an accurate fashion. One or more guide rods may interface with one or more support springs and an adjustable screw, as is illustrated. The adjustable screw may be coupled to a channel that facilitates movement of device 10. Thus, a simple adjustable screw or an electronic component may be used to achieve such positioning of device 10. The adjustable screw allows the loading dock to move up and down for precise positioning and/or engagement of tips 18 of device 10.

Figure 7A:
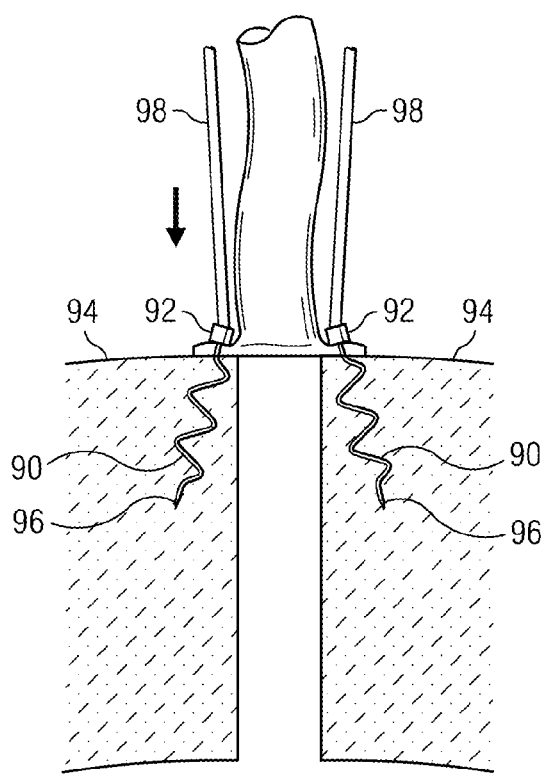
FIGS. 7A-D are simplified schematic diagrams of a fastening configuration that may be used in conjunction with the device.
Figure 7B:
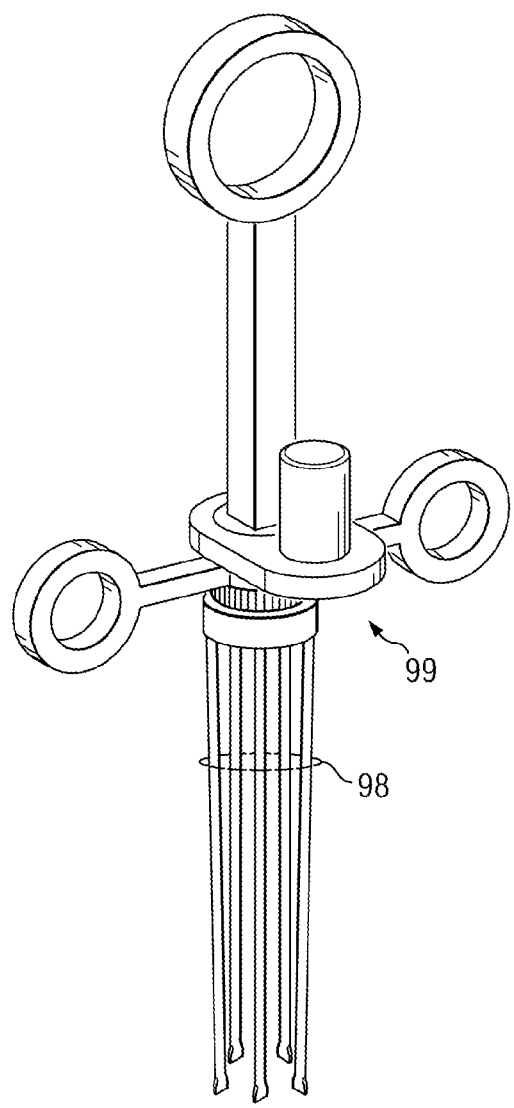
Figure 7C:
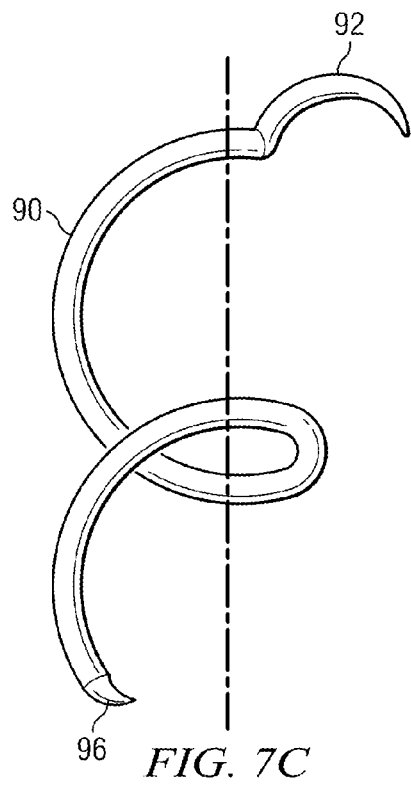
Figure 7D:
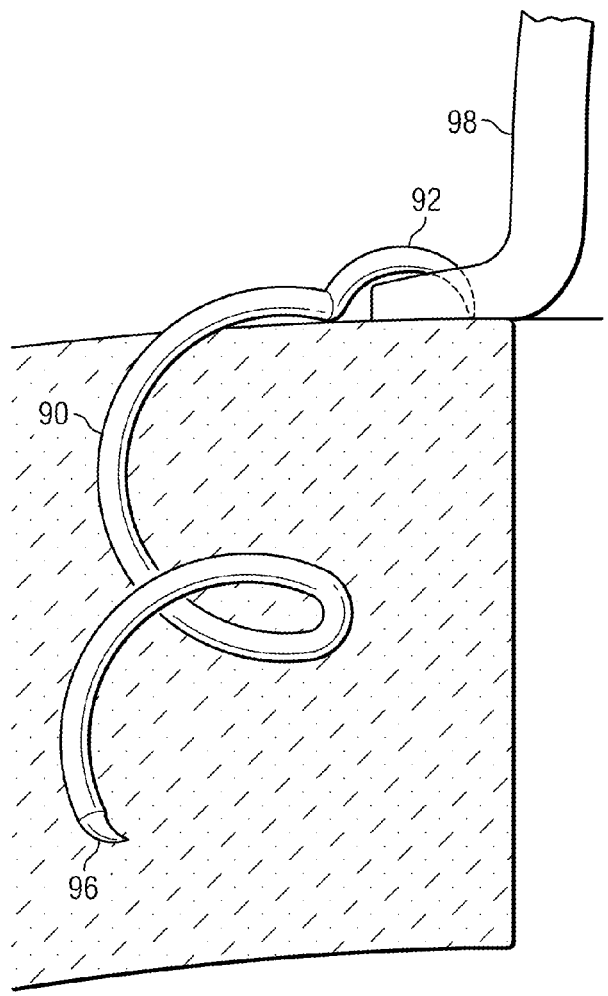

FIG. 7A-D illustrates a new fastening approach for securing the vein to an aortic wall. FIG. 7A illustrates a set of closures 90, which represent mechanical fastening elements that may be twisted such that they are secured within an aortic wall 94. FIG. 7B illustrates an actuator 99 that may be used in conjunction with closures 90. FIG. 7C illustrates one specific design of closures 90 and FIG. 7D illustrates a more detailed view of the fastening configuration of closures 90. In one embodiment, closures 90 are formed in a spiral or a corkscrew design, as illustrated by FIG. 7C. Alternatively, any appropriate design (e.g. straight, zigzag, curved, etc.) can readily be used to make the attachment between the vein and the aorta.

Closures 90 may be clips, wires, nails, screws, pins, hooks, clasps, ties, or any other element that is operable to affix closures 90 in place. Closures 90 may be constructed of steel, plastic, titanium, or any other material, composite, or element that is suitable for such an application. Each closure 90 may include a head 92, which serves as an interface that can be manipulated to yield a twisting motion or a rotation for closures 90. Head 92 represents a suitable flange of some type and it can receive any tool (or be manipulated by hand) in order to secure closures 90 at their designated locations.

In operation of an example embodiment, each closure 90 may be driven into the aortic wall (using heads 92) at an angle (e.g. approximately 10-15 degrees), as is illustrated in FIGS. 7A and 7D. Alternatively, closures 90 can be driven into aortic wall 94 at any other suitable angle. Each closure 90 may also be provided with a tip 96, which is sharp enough to easily pierce aortic wall 94 with minimal effort. Heads 92 may be flush with aortic wall 94 once driven to a suitable length. Note that closures 90 are designed such that they can be driven to a designated length (e.g. 2 millimeters): potentially by using a prescribed number of turns with one or more mating elements 98. This would allow for the vein to be suitably secured to aortic wall 94, while preventing closures 90 from exiting aortic wall 94. In one embodiment, closures 90 include an angled head 92 (illustrated by FIG. 7C), which can offer a self-locking feature for the suturing operations. Other heads are certainly within the broad scope of the present invention.

FIG. 7B is a simplified diagram of an automated approach of the example of FIG. 7A. FIG. 7B includes actuator 99, which includes one or more mating elements 98. Mating elements 98 provide a convenient interface between the surgeon and closures 90. In this particular embodiment, each of mating elements 98 includes a head (e.g. a standard flat-head screwdriver) that may be used to produce torque such that closures 90 move in a downward direction. Legs 16 of device 10 may include an adapter (not shown) that can be used in conjunction with (or without) mating elements 98. This could accommodate such a securing operation and allow for closures 90 to turn rotationally.

Note that any of the previously discussed materials could be included in a given kit, which could ostensibly be provided to a physician who is responsible for performing a bypass procedure. A basic kit could include a clamp 70 with a stand 20 and device 10. The kit could also include an actuator (as described) to automate some of the processes outlined herein. The kit could further include one or more closures 90 for suturing or affixing the vein or tube. Any of these components may be manufactured based on particular specifications or specific patient needs. The present invention contemplates considerable flexibility in such components, as any permutation or modification to any of these elements is clearly within the broad scope of the present invention.

It is important to note that the stages and steps in the preceding FIGURES illustrate only some of the possible scenarios that may be executed by, or within, the architecture of the present invention. Some of these stages and/or steps may be deleted or removed where appropriate, or these stages and/or steps may be modified or changed considerably without departing from the scope of the present invention. In addition, a number of these operations have been described as being executed concurrently with, or in parallel to, one or more additional operations. However, the timing of these operations may be altered considerably. The preceding example flows have been offered for purposes of teaching and discussion. Substantial flexibility is provided by the proffered architecture in that any suitable arrangements, chronologies, configurations, and timing mechanisms may be provided without departing from the broad scope of the present invention.

Note also that the example embodiments described above can be replaced with a number of potential alternatives where appropriate. The processes and configurations discussed herein only offer some of the numerous potential applications of the device of the present invention. The elements and operations listed in FIGS. 1-7D may be achieved with use of the present invention in any number of contexts and applications. Accordingly, suitable infrastructure may be included within device 10 (or cooperate with device 10) to effectuate the tasks and operations of the elements and activities associated with managing a bypass procedure.

Although the present invention has been described in detail with reference to particular embodiments in FIGS. 1-7D, it should be understood that various other changes, substitutions, and alterations may be made hereto without departing from the sphere and scope of the present invention. For example, although the preceding FIGURES have referenced a number of components as participating in the numerous outlined procedures, any suitable equipment or relevant tools may be readily substituted for such elements and, similarly, benefit from the teachings of the present invention. These may be identified on a case-by-case basis, whereby a certain patient may present a health risk factor while another (with the same condition) may not. Hence, the present device may be designed based on particular needs with particular scenarios envisioned.

It is also imperative to note that although the present invention is illustrated as implicating a bypass procedure, this has only been done for purposes of example. The present invention could readily be used in any vein, artery, tube, or vessel attachment procedure and, accordingly, should be construed as such. As used herein in this document, all of these items may be generically referred to as a conduit, which may be harvested from a mammal or manmade. The present invention may easily be used to provide a viable vascular management solution at various locations of the mammalian anatomy, which are not necessarily illustrated by the preceding FIGURES. Hence, while the system is described as being applicable in end-to-side anastomosis (with particular attention being given to end-to-side anastomosis for CABG surgeries using venous or arterial grafts to the aorta), device 10 can be used in any other scenario in which a vein needs to be attached in some fashion.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims. In order to assist the United States Patent and Trademark Office (USPTO) and additionally any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of filing hereof unless the words "means for" are specifically used in the particular claims; and (b) does not intend by any statement in the specification to limit his invention in any way that is not otherwise reflected in the appended claims.

What is claimed is:

1. A method to be completed in a vascular environment, comprising:
   harvesting a conduit;
   loading the conduit onto a device wherein the device includes:
      a handle; and
      two or more legs operable to move in response to a force being applied to the handle, wherein each of the legs includes a respective tip and an outwardly curved portion, wherein the curved portions collectively form a bell shape and the tips are disposed distally of the bell shape, and wherein the legs are operable to extend radially outward from an axis about which the tips are disposed and to contract radially inward toward the axis in order to expand and compress an end of the conduit when the end of the conduit is loaded on the tips;
   positioning the tips of the device in a hole of an aorta; and
   extending the tips such that at least a portion of the tips engage a wall of the aorta, wherein the end of the conduit forms a lip on an outer surface of the aorta around the hole.

2. The method of claim 1, further comprising:
   sizing the hole, which is to be made in the aorta, based on one or more graduations provided on a stand, which temporarily holds the conduit.

3. The method of claim 1, further comprising:
   coupling the conduit to the aorta.

4. The method of claim 3, wherein the coupling includes driving one or more closures into the aorta while the device stabilizes the conduit.

5. The method of claim 1, further comprising:
loading the conduit onto a stand; and
removing the conduit from the stand using the device.

6. The method of claim 1, further comprising:
contracting the tips of the device before the tips are positioned in the hole of the aorta, wherein the end of the conduit is compressed when the tips are contracted.

7. A method comprising:
loading an end of a conduit onto a plurality of opposing tips of a device that converge toward an axis, wherein the device and the conduit are configured for use in a vascular environment, wherein the device further includes:
a handle; and
a plurality of legs, each terminating at one of the opposing tips, wherein the opposing tips are operable to be radially extended away from the axis in response to a force being applied to the handle and operable to be radially contracted toward the axis in response to another force being applied to the handle, wherein the end of the conduit is expanded and compressed as the tips are extended and contracted, respectively;
advancing the tips longitudinally beyond the end of the conduit to expose the tips;
contracting the tips of the device before the tips are positioned in a hole of an aorta, wherein the end of the conduit is compressed when the tips are contracted;
positioning the longitudinally advanced tips in the hole of the aorta; and
extending the tips of the device such that at least a portion of the tips engage an aortic wall defining the hole of the aorta, wherein the end of the conduit forms a lip on an outer surface of the aorta around the hole.

8. The method of claim 7, further comprising:
loading the conduit onto a stand; and
positioning the conduit adjacent a graduation having a size corresponding to a diameter of the conduit.

9. The method of claim 8, wherein the hole in the aorta is cut based on the diameter of the conduit.

10. The method of claim 7, further comprising:
coupling the conduit to the aorta.

11. The method of claim 10, wherein the coupling includes driving one or more closures into the aorta while the device stabilizes the conduit.

12. The method of claim 7, further comprising:
loading the end of the conduit onto a stand, wherein at least a portion of an interior surface of the conduit engages the stand;
positioning the tips of the device around an exterior surface of the end of the conduit;
piercing the end of the conduit with the tips; and
removing the conduit from the stand using the device.

13. A method to be completed in a vascular environment, comprising:
harvesting a conduit;
loading the conduit onto a stand;
loading the conduit onto a device wherein the device includes:
a handle; and
two or more legs operable to move in response to a force being applied to the handle, wherein each of the legs includes a respective tip and an outwardly curved portion, wherein the curved portions collectively form a bell shape and the tips are disposed distally of the bell shape, and wherein the legs are operable to extend radially outward from an axis about which the tips are disposed and to contract radially inward toward the axis in order to expand and compress an end of the conduit when the end of the conduit is loaded on the tips; and
removing the conduit from the stand using the device.

* * * * *